United States Patent
Wolff et al.

[11] 4,016,111
[45] Apr. 5, 1977

[54] NON-BURNING, CLASS 1 RATING, FOAMS AND A METHOD OF PRODUCING SAME

[75] Inventors: Per Lind Wolff, Birkeroed, Denmark; John Arthur Gooch Gent, Liphook, England

[73] Assignee: Koninklijke Emballage Industrie Van Leer B.V., Amstelveen, Netherlands

[22] Filed: Apr. 1, 1975

[21] Appl. No.: 564,184

[30] Foreign Application Priority Data

Apr. 4, 1974 United Kingdom ............ 15067/74

[52] U.S. Cl. .......................... 260/2.5 F; 106/15 FP; 260/45.75 R; 260/72 R; 260/DIG. 24
[51] Int. Cl.² ............................................ C08J 9/00
[58] Field of Search ................. 260/2.5 F, DIG. 24, 260/45.75, 51.5, 72; 106/15 FP

[56] References Cited

UNITED STATES PATENTS

| | | | |
|---|---|---|---|
| 3,006,871 | 10/1961 | Sunderland | 260/2.5 F |
| 3,740,358 | 6/1973 | Christie et al. | 260/2.5 F |
| 3,919,127 | 11/1975 | Larsen et al. | 260/2.5 F |

FOREIGN PATENTS OR APPLICATIONS

| | | |
|---|---|---|
| 1,432,889 | 3/1965 | France |
| 1,248,756 | 10/1971 | United Kingdom |
| 942,845 | 11/1963 | United Kingdom |

OTHER PUBLICATIONS

Frisch et al., *Plastic Foams* II, p. 690, (Dekker, 1973).
Benning, *Plastic Foams* I, pp. 471–472, (Wiley, 1966).
Benning, *Plastic Foams* II, p. 132, (Wiley, 1966).

*Primary Examiner*—Murray Tillman
*Assistant Examiner*—T. De Benedictis, Sr.
*Attorney, Agent, or Firm*—Lawrence Rosen; E. Janet Berry

[57] ABSTRACT

Method of preparing foamed solid aminoformaldehyde furfurylalcohol products by polymerizing a liquid furfurylalcohol containing aminoformaldehyde resin composition in the presence of an acid, characterized in using as a starting material a resin composition containing 15–90% by weight of total free and bound furfurylalcohol and having an urea:formaldehyde molar ratio of 1:1 to 1:5 and at least 10 parts by weight of a boron compound per 100 parts by weight of said resin, the boron compound being present in an amount sufficient so that the foam product will pass the muffle furnace test at 500° C., and has no second exotherm at 200° C. The boron compound can be selected from the group consisting of boric acid, boron oxide, borax, boric acid esters, boron tribromide, boron trichloride, boron nitride, boron phosphate, boron trifluoride etherate, boron trifluoride methanol, boron trifluoride monoethylamine, complexes of boric acid with polyhydroxyl compounds, and mixtures thereof.

9 Claims, 4 Drawing Figures

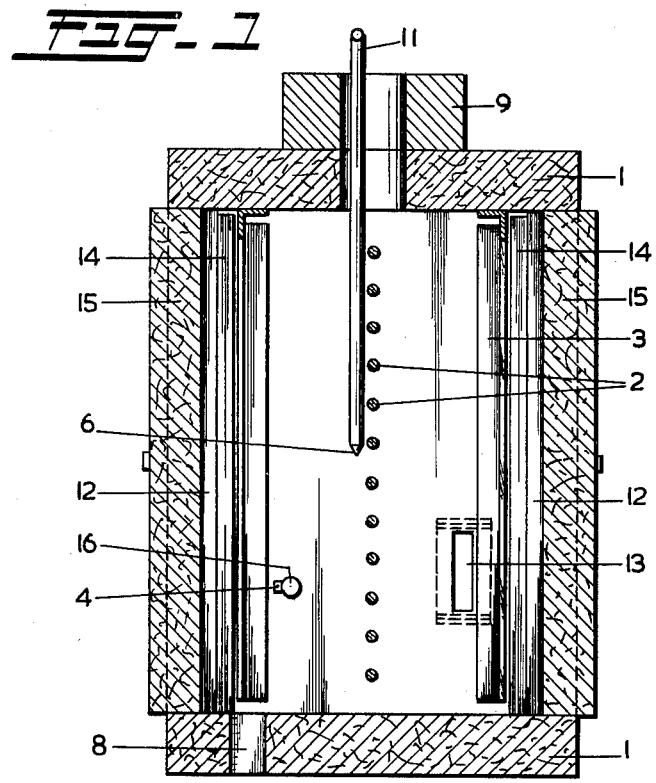
FIG. 1
FIG. 4
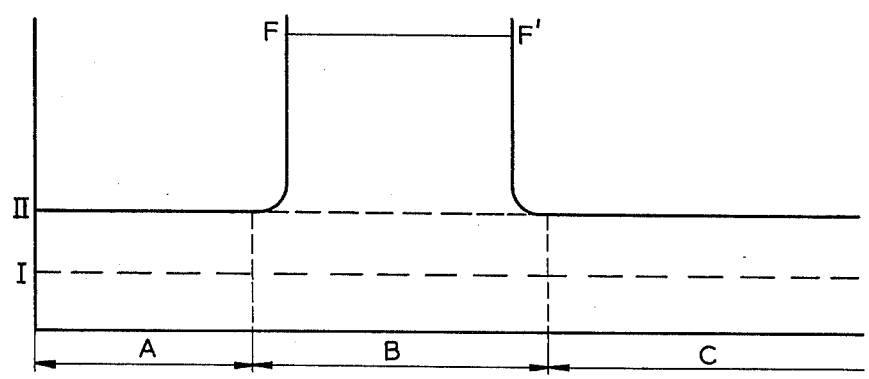

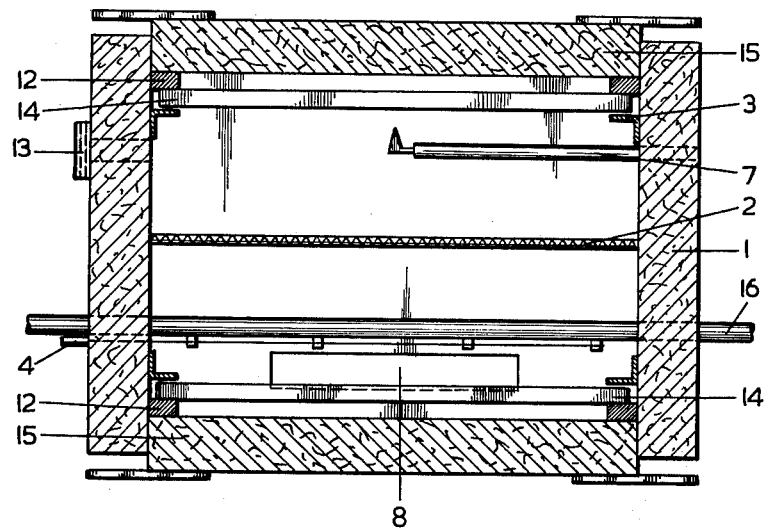
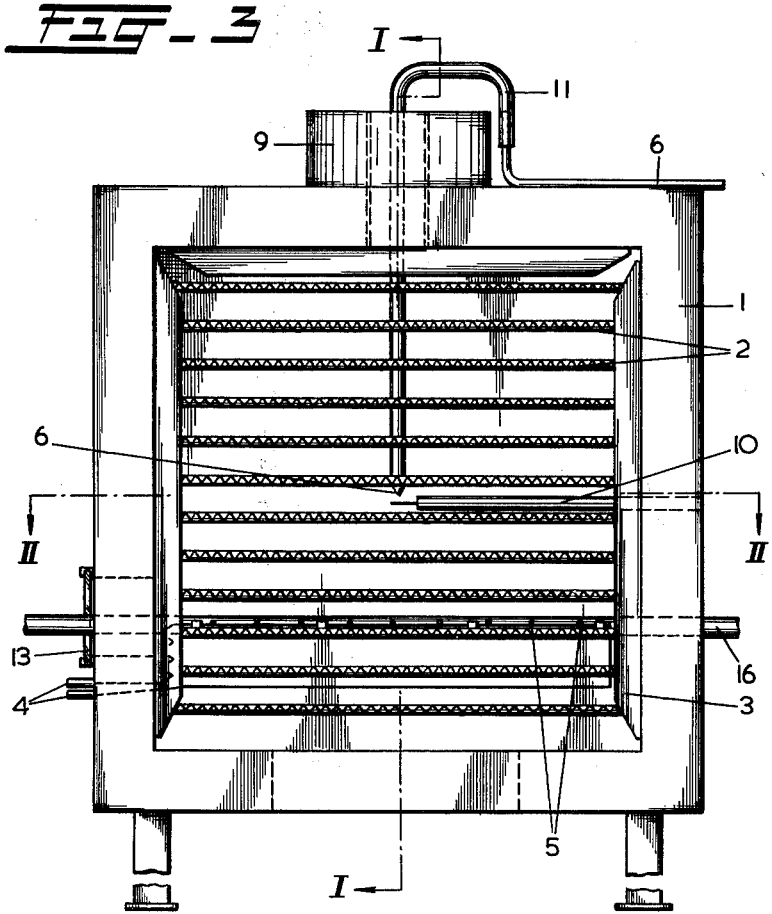

NON-BURNING, CLASS 1 RATING, FOAMS AND A METHOD OF PRODUCING SAME

The present invention relates to a method of preparing foamed solid aminoformaldehyde furfurylalcohol products by polymerizing a furfurylalcohol containing aminoformaldehyde liquid resin composition in the presence of an acid.

In British patent 942,845 a method of preparing such foamed solid aminoformaldehyde furfurylalcohol products is disclosed, wherein a furfurylalcohol containing aminoformadlehyde composition is polymerized in the presence of a strong acid. Due to their low thermal conductivity in combination with non-inflammability as determined by older fire tests such as ASTM 1692, the products obtained according to said method are proper for thermal insulation. However, they cannot be considered as non-inflammable when tested by more severe fire tests such as the NEN 1076, part C, flash-over test, since they are not able to pass said test with a class 1 rating.

Description of the NEN 1076, part C test relating to contribution of flash-over and flammability 1. Purpose.

This part comprises the method for determination of the flash-over intensity, in order to be able to determine the contribution of materials to the occurrence of flash-over and their flammability. Materials are classified according to their flash-over intensity.

2. Principle

To determine the flash-over intensity, two samples to be tested are erected vertically and parallel to each other in a test box. They are exposed to such an amount of heat, that flash-over, if possible, occurs, from one testing sample to the other. The amount of heat applied per second and per square centimeter on the surface of the testing sample to give flash-over in exactly 15 minutes, assesses the classification. This heat is called the flash-over intensity and can be considered as a measure for the contribution to flash-over and the non-flammability of the concerned material.

3. Testing samples 3.1 Dimensions

The testing samples shall have an area of 300 millimeters × 300 millimeters.

Thickness shall be the normal thickness of the material.

3.2 Number

Number of testing samples necessary to determine the flash-over intensity is normally 10.

4. Preparation of the testing samples

Materials shall be offered to testing in the condition in which they are used in practice. Before testing, the humidity of the testing samples shall be in equilibrium with that of air with a temperature of 10° to 20° C and a relative humidity of 55 to 65 percent. If competent authorities judge it necessary, from a few testing samples shall be determined the flash-over intensity after being submitted to one or more aging-, weathering- or other tests, this to be pointed out by said authorities.

5. Apparatus

To determine the flash-over intensity an apparatus is used as shown in FIG. 1. The apparatus is made from asbestos-panels, having a thickness of 34 millimeters (1). In the centre incandescent wire is spirally wound on 12 quartz rods (2). Electric current can be lead through these wires. The energy output can be expressed in cal/cm$^2$ sec. and is found by dividing the supplied energy expressed in calories per second by the area of the cross-section of the test box parallel to the testing samples (900 cm$^2$). The incandescent spiral wire is made from chromium-nickel steel with a dimater of 0.6 mm. Each of the testing samples 14 can be clamped between steel supports 3 and a loose panel of asbestos 15 having a thickness of 34 mm. On these asbestos panels are attached along the vertical sides two strips of asbestos 12 having a thickness of 10 mm. Thus the testing sample and the asbestos panel are separated by an air cavity of 10 mm width. One of the test samples is exposed to 9 gas flames, each having a length of 20 mm directed perpendicular to the testing sample, whilst the distance between the nozzles is 30 mm, each nozzle 5 having a diameter of 1 mm.

The nozzles in the gas supply tube 16 are positioned at a height of 75 mm above the bottom of the box. By means of thermo-couples on two places the temperature can be measured: in the centre of the test box 6 and in front of the testing sample, which is not exposed to the gas jets, at a distance of 5 millimeters from the surface of the testing sample 7. Other characteristics of the test box are shown in FIG. 1, such as venting holes in the bottom 8, a funnel 9, thermocouple tubes 10, 11, a screened off observation hole 13 and a glowing wire 4 to ignite the supplied gas.

6. Procedure

The closed test box has to be warmed up by means of the gas jets until the temperature has become constant inside. This can be controlled with the thermo-couple in the centre of the box. Attach with help of the asbestos panel the sampe that is not to be exposed to the gas jets and put the second test sample in such a way that this closes the box partially, but does not touch the gas jets. Attach the second sample with the second asbestos panel as soon as the inside temperature has risen to 60° C and connect an electric power supply to the incandescent wires 2. When testing materials which develop extinguishing gases (so called self-extinguishing materials), the electric glowing wire (power consumption 20 Watts) has to be connected to a power supply, to prevent extinguishing of the gas jets. When testing materials which distort or malt, a wire netting (mesh size 12 mm, thickness 0.8 mm) has to be pinched between the steel supports 3 and the testing sample, or the sample has to be glued (if possible) on an asbestos panel having a thickness of at least 3 mm, this to prevent sagging. Determine the change in temperature of the thermo-couple which is placed in front of the test sample not exposed to the gas jets by measuring the temperature at least every minute until flash-over has occurred, or for a maximum time of 30 minutes measured from the time the second sample has been attached. When testing materials which melt and drip to the bottom of the box during the test, the same procedure must be used.

Flash-over is to be established visually by looking through the loophole 13 or to be deduced from the temperature change of the thermo-couple in front of the testing sample not exposed to the gas jets.

Flash-over may be assumed if the testing sample not exposed to the gas jets is burning or, if not visually apparent burning, the temperature of the concerning thermo-couple has risen within 1 minute by 15° C more than in the preceding minute.

When at an energy supply of 0.05 cal/cm² sec. flashover has occurred within, or exactly in 15 minutes, the test is finished.

Is the energy supply more than 0.05 cl/cm² sec. and a flash-over time has been found in the first test of less or more than 15 minutes, then the test has to be repeated for other amounts of energy per square centimeter until from two or more tests, by graphic inter- or extrapolation, the exact amount of energy can be deduced, at which in exactly 15 minutes flash-over will occur.

7. Classification

Materials can be classified concerning their flashover intensity F as shown in the following table.

Table

| | | |
|---|---|---|
| Class I | F ≥ 0.4 cal/cm² sec. | Material does not contribute to flash-over |
| Class II | 0.2 ≤ F < 0.4 cal/cm² sec. | Material does contribute slightly to flash-over |
| Class III | 0.05 ≤ F < 0.20 cal/cm² sec. | Material does contribute appreciably to flash-over |
| Class IV | F < 0.05 cal/cm² sec. | Material does contribute strongly to flash-over |

Testing several commercially available thermal insulation materials, it appeared that none of them passed said NEN flash-over test. Also the non-inflammable materials disclosed in applicant's British patent application 39707/72 are not able to pass the NEN flashover test with a class 1 rating.

Boron compounds are known to improve the performance of various foams in fire tests such as ASTM 1692, ASTM D 653-44, ASTM E 162 radiant panel test, or the Butler chimney flammability test for cellular plastics. The latter is described in detail in the Journal of Cellular Plastics, November 1967.

In the Journal of Cellular Plastics, September 1970, pages 215 a.ff., Carlos J. Hilado et al describe the effect of boric acid, boric anhydride, sodium borate, zinc borate, and a number of organic boron compounds, on the inflammability of rigid polyurethane foams. The boron compounds are used in concentrations up to 40 parts by weight per hundred parts by weight of polymer. It is found that although the boron compounds may reduce the burning rate and burning extent, none of the compositions are non-inflammable or free of flash-over.

In U.S. Pat. No. 3,740,358 is disclosed that boric acid, boric oxide, and boron polyol complexes can be used to render a phenolic foam-non-punking.

The punking properties of the phenolic foams are the properties of continuing the glow and combust without a visible flame despite the removal of the external heat source. Although the boron compounds disclosed by U.S. Pat. No. 3,740,358 may render a phenolic foam non-punking, said foam will still be combustible and show flash-over when tested in the above NEN test.

Since there is a serious demand for materials meeting the high requirements of the abovementioned NEN test, and current as well as further regulations in this field will require a foam material for use in buildings to be free of flash-over as determined by said NEN test and tests compared therewith such as Williamson's Corner Test and the Factory Mutual Channel Test, it is very interesting to find a material passing said test.

Surprisingly it was found now, that a material passing said test may be obtained by polymerizing in the presence of an acid a resin composition containing 15 to 90% by weight of free alternatively bound furfurylalcohol and having a urea: formaldehyde molar ratio of 1:1 to 1:5 and incorporating at least 10 parts by weight of a boron compound per 100 parts by weight of said resin composition to being it in a condition so that it will pass the muffle furnace test at 500° C as herein described.

BRIEF DESCRIPTION OF THE DRAWINGS

The invention will be more fully understood by reference to the accompanying drawings, FIGS. 1 to 4. Briefly, FIGS. 1, 2, and 3 show different views of the apparatus used to test the flash-over intensity as described above on pages 3 and 4. FIG. 4, on the other hand, is a graph showing the improvements achieved in the practice of the present invention as described on page 14 below. More specifically, the self-extinguishing level II is highest when the composition contains boric acid and is particularly oustanding in connection with its use with aminoformaldehyde furfurylalcohol foams.

THE MUFFLE FURNACE TEST

Apparatus

The muffle furnace test is performed in an apparatus consisting of a laboratory horizontal muffle furnace (type Nr. 170 from Heracus, Germany) having a depth of 300 mm, a width of 170 mm and a height of 100 mm. All dimensions measured inside the furnace space. The furnace is heated by means of electric heating elements having a total consumption of 3000 Watts. The temperature is controlled by means of a thermostate capable of regulating the temperature inside of the furnace with an accuracy of approximately 7.5° C in the range of from 500° to 550° C.

A jig for mounting the samples during the test consists of a flat rectangular frame made from 9 mm stainless steel tubing. The ouside dimensions of the frame are 160 × 250 mm. On one of the short sides of this frame a cubical sample holder made from thin stainless wire mesh is mounted. This wire mesh holder is in the shape of a box having internal dimensions of 32 × 32 × mm, and is open upwards and towards the centre of the frame.

From the bottom of the sample holder protrudes a small iron konstantane thermo-couple protected by a 2.5 mm diameter stainless steel tube. When the foam sample to be tested is placed in the sample holder, this thermo-couple will be in the centre of the sample and will record the temperature in the centre of the sample.

Another thermo-couple is placed just outside the centre of the left side of the sample holder. This thermo-couple is unprotected and will record the furnace temperature very close to the surface of the sample during the test. Both thermo-couples are made from very thin wires (maximum 0.25 mm) to assure rapid response during the test.

A 1.5 mm bore stainless steel tube comes up from the frame behind the sample holder, and the end of the this tube is bent horizontally over the sample holder so that the tip is 25 mm from the top of the sample. During the test natural gas is fed through this pipe to give a horizontal pilot flame 10 mm long. 25 mm over the top of the sample this flame will ignite any flammable material given off from the sample during the test.

The two thermo-couples are connected to a two point recorder with a full scale deflection of 250 mm, a sensitivity of 2 mV per cm, and a paper speed of 60 mm/min.

Also an event marker is provided, which allows the operator to mark the start and stop of any flashing or burning occurring during the test.

Calibration

Prior to any test the furnace should have been at the test temperature with the furnace door open for at least 6 hours.

A small cube 30 × 30× 30 millimeters of mineral wool, density 60 kg/m³, is placed in the sample holder. The jig is pushed into the furnace so that sample holder is in the correct position close to the back wall of the furnace.

The temperature of the two thermo-couples is now recorded and corrections in the furnace temperature are made if necessary. When the conditions are correct, the temperature recorded in the centre of the dummy sample will be equal to said temperature plus minus 6° C.

After calibration the jig is removed from the furnace and allowed to cool below 200° C before any test sample is placed in the sample holder.

Test samples

The test samples shall have the dimensions of 30 × 30 × 30 millimeters.

Before testing, the humidity of the test samples shall be in equilibrium with that of air with a temperature of 18°–22° C and a relative humidity of 55 to 65%.

Test procedure

The sample is placed in the sample holder and pressed down until the thermo-couple is in the centre of the sample. If necessary a small hole in the sample for this thermo-couple should be bored in advance.

The pilot flame is ignited, and the jig is rapidly pushed into the furnace so that sample is in the correct position close to the rear wall of the furnace, and a mark is made on the recorder to indicate the start of the test.

The sample is now closely observed, and any burning or sample or flashing of volatiles around the sample is recorded with the event marker.

The test is continued for at least 5 minutes, or for materials in which the temperature in the centre of the sample rises over the furnace temperature until the centre temperature is again going down. The maximum temperature reached during the test is noted.

After the test the jig is removed from the furnace and allowed to cool below 200° before being used for the next test.

Evaluation of test results

A sample showing no flash or burning is considered as having passed the muffle furnace test. If the test temperature is 500° C or higher, then the sample must be considered as having a high degree of non-flammability and may pass official tests such as the NEN flashover thest described above.

It has been found that among the materials passing the muffle furnace test at 500° C, a further selection can be made based on the maximum temperature recorded during the test. Those materials showing lower maximum temperature such as temperatures below around 550° C, generally show the better performance in other fire tests, and hence such materials are particularly preferred.

Proper resin compositions containing furfurylalcohol are: urea formaldehyde furfurylalcohol resins and urea formaldehyde resins dissolved in furfurylalcohol. Also furfurylalcohol prepolymers commercially sold as "furan resins" may be used. They are generally of a type in which the furfurylalcohol monomer units have been bound together under loss of the alcohol group. They contain a number of furan rings via a methylene group. The amount of furfurylalcohol prepolymer which can be tolerated will depend on the level and type of boron compound used in the formulation, on the type of UFF resin as well as on the degree of polymerisation of the furfurylalcohol polymer. Generally it is preferred to use less than 40 percent furfurylalcohol in this form.

The preferred resin composition is a UFF resin prepared from a mixture containing urea formaldehyde and 15 to 90 parts by weight furfurylalcohol, with the understanding that the molar ratio between urea and formaldehyde will be in the range from 1:1 and 1:5. Obviously the urea may be replaced by or combined with thiourea and/or melamine.

Preferred ratios between urea and formaldehyde are in the range from 1:1.5 to 1:4, with the ratios in the range 1:1.5 to 1:2.5 being particularly preferred, as giving optimum balance between fire- and mechanical properties. The contents of bound and/or free furfurylalcohol is generally between 15 and 90 parts by weight per 100 parts of resin. The preferred range is between 25 to 70 percent and particularly preferred in the range of 25 to 50 percent giving the optimum balance between foaming characteristics and fire resistance.

A resin composition that in absence of a boron compound can be converted into a foam showing substantially no second exotherm at 200° C, e.g. a maximum temperature of about 225° C when tested according to the undermentioned second exotherm test, is preferred.

Also resin compositions that in presence of at least 10 parts by weight of a boron compound per 100 parts by weight of resin can be converted into a foam showing substantially no second exotherm at 200° C, e.g. a maximum temperature of 225° C, tested according to the undermentioned second exotherm test, are very useful.

The test for determining whether the second exotherm reaction will be developed is carried out in the following way.

A sample is cut with dimensions 6 × 6 × 6 cm. The sample is placed in the middle of an oven, the temperature of which is kept at 200° C. A thermo-couple is inserted in the middle of the sample and the temperature of the foam recorded. In foams having a second exotherm, the temperature of the foam will rise above 200° C and the maximum temperature is noted.

Formulations which develop low exotherms generally require less boron compounds to be free of flash-over, whereas foams having higher exotherms can be made free of flash-over only if higher amounts or a more effective type of boron compounds are used.

The boron compounds that may be used may be of an inorganic as well as of an organic nature. Boric acid and boric oxide are the preferred compounds, but also borax, boric acid esters, boron tribromide, boron trichloride, boron nitride, boron phosphate, boron trifluoride etherate, boron trifluoride methanol and boron trifluoride monethylamine may be used, as well as complexes of boric acid with polyhydroxyl compounds and mixtures of boron compounds.

In the present method a variety of blowing agents and combinations of blowing agents may be used, e.g. Freon 113, Arcton 11, dimethoxyethane, methylenechloride, 1.1.1-trichloroethane or pentane. They are generally used in minor amounts such as between 2 and 40 parts per 100 parts of resin.

Proper surfactants are those typically used in polyurethane and ureaformaldehyde foams, like DC 193, and non-silicones like LK 221. The surfactants are generally used in minor parts such as 0.005 to 5 parts per 100 parts of resin depending on the efficiency of the specific surfactant or blends of surfactants.

Typical examples of proper acids are ortho-phosphoric acid, polyphosphoric acid and sulphuric acid. Generally an oxy-acid of phosphorus is used if desired in combination with another acid, such as sulphuric acid or para-toluene sulphonic acid, but an oxy-acid of phosphorus can be used as the only acidic catalyst. If desired the acidic compound may be used in combination with an alcohol or hydroxyaldehyde as glucose. A very goodd combination is aqueous phosphoric acid containing 30–90 parts by weight of $H_3PO_4$ and up to 50 parts by weight of glucose. The catalyst is generally used in minor amounts such as between 2 and 20 parts on 100 parts of resin.

Preferred alcohols are 1.4-butanediol and propane-2-ol. Other preferred alcohols are the polyglycols.

Conventional polymerization and foaming procedures are employed in preparing the foams of the present invention and it is to be understood that the use of these procedures is not a critical feature.

In general however, the polymerization is accomplished by bringing the feed materials together at ambient temperature or within the range of 10° to 40° C, and mix them intimately. The mixing may be done at ambient pressure or at elevated pressure up to 20 atmospheres or higher.

The blowing agent or other additives if employed, may be added to the feed materials or as a separate stream during the mixing. The mixed reaction materials are then poured into open or closed molds and allowed to polmyerize into the final solid state.

The polymerization may be started under ambient temperature and pressure conditions, alternatively heat may be applied to or extracted from the mold to initiate or control the initial rate of polymerisation.

During the polymerization the heat of reaction will increase the temperature of the mixture and the blowing agent(s) will expand the material into the desired foams state. The temperature during the reaction may rise up to temperatures between 40° and 130° C.

After the initial setting of the foam material the cure may be completed by keeping the material at an elevated temperature for a period of time which may vary from 15 minutes to 10 hours depending upon reactivity of the feed materials.

It appears that completion of the foaming reaction is essential for obtaining a good performance in fire tests, and said completion may be achieved only if the resin and the acid used are sufficiently compatible and are able to form an intimate mixture for a long period during the foam formation.

If the resin and the acid have insufficient compatibility, or if during the cure they become wholly or partly incompatible and separate out into macrophases, then the reaction will not go to completion and the foam will have a second exotherm reaction and show poor performance in fire tests.

The gist of the invention is that a very special selection from known aminoformaldehyde compositions containing furfurylalcohol is polymerized in the presence of an acid and incorporating a boron compound to bring it in a condition so that it will pass the described muffle furnace test. Generally the incorporation of boric acid yields an improvement in non-inflammable properties of foamed materials, but said improvement is of such a limited scope that the foams obtained do not pass the NEN 1076 flash-over test. This is elucidated in FIG. 4, wherein I means the self-extinguishing level without addition of boric acid, II is the level achieved by incorporating boric acid in phenolic foams (A), aminoformaldehyde furfurylalcohol foams (B) and other foams (C). The area of the invention is indicated by F—F'.

The surprising effect achieved according to the present invention appears from the examples.

It appears that all compositions passing the flash-over test contain at least about 10 parts by weight of a boron compound per 100 parts by weight of resin, but that not all compositions containing said amount do pass the flash-over test.

It further appears that all compositions passing the muffle furnace test will pass the NEN flash-over test and all compositions failing in the muffle furnace test will not pass the NEN flash-over test.

The invention is elucidated in the undermentioned examples, wherein the amounts of the components in the compositions are indicated in parts by weight, if no other indication is used explicitely.

EXAMPLE I

A series of foams was prepared using the formulations stated in Table 1.1. The foams were tested according to NEN test No. 1076, part C. The test results are stated as the time elapsed before a flash-over occurs at an energy input of 0.4 cal/cm² sec. The requirement for a class 1 rating in the test is that this time should exceed 15 minutes. In addition, results of muffle furnace tests and second exotherm tests are stated.

Table 1.1.

| Foam No. | 1.1 | 1.2 | 1.3 | 1.4 | 1.5 |
|---|---|---|---|---|---|
| 1) UFF resin | 60 | 60 | 60 | 100 | 100 |
| 2) Furan resin | 40 | 40 | 40 | — | — |
| Silicone surfactant (DC 193) | 1 | 1 | 0.8 | 1 | 1 |
| Boric acid | 30 | 30 | 25 | 35 | 35 |
| Borax | — | — | — | –2 | –3 |
| Blowing agent (Freon 113) | 6 | 6 | 6 | 6 | 1 |
| 3) Fyrepruffe | — | — | 25 | — | — |
| Catalyst: Orthophosphoric acid, 89 o/o, parts by weight | 9.1 | 7.2 | — | 9.7 | 9.4 |
| Polyphosphoric acid | — | — | 10 | — | — |
| Isoproapnol | — | — | 6 | — | — |
| 1.4 Butanediol | 2.6 | — | — | — | — |
| Methanol | — | 2 | — | — | — |
| Water | 2.6 | 2.0 | — | 4 | 5.2 |
| Glucose | 9.7 | 10.2 | — | 10.7 | 10.4 |
| Muffle furnace test 500° C, flash +/− | + | + | + | — | — |
| 2nd exotherm at 200° C | 450 | 227 | 442 | 206 | 206 |
| NEN 1076 part C test, time to flash-over (min., sec.) at 0.40 cal/cm² sec. | 8.40 | 13.50 | 12.35 | >18 | >25 |

Table 1.1.-continued

| | |
|---|---|
| | and 15.30 |
| at 0.5 cal/cm² sec. | >15 |
| at 0.6 cal/cm² sec. | >15 |

1) Borden TN1
2) Synphorm P 490
3) A commercial fire retardant containing ammonium phosphate and ammonium sulphate.

Foam 1.1 does not pass the muffle furnace test nor the NEN 1076 test although it contains 30 parts boric. This is consistent with the high amount of furan resin used in the preparation of the foam, which makes it difficult to obtain a complete cure, as is evident from the high temperature reached in the second exotherm test.

Foam 1.2 is made with another catalyst, and the second exotherm is now much lower. This foam shows a very brief flash in the muffle furnace test and is almost passing the NEN test.

Foam 1.3 shows that conventional fire retardant cannot produce the desired effect.

Finally foams 1.4 and 1.5 show the superior performance in the NEN 1076 test of urea-formaldehyde-furfurylalcohol foams to which sufficient boric acid has been added to make them pass the muffle furnace test.

EXAMPLE II

Foamed materials were prepared using the formulations given in table 2.1. The resin blend was pumped to a mixing chamber in which it was intimately mixed with the catalyst. The mixture was poured into a mould and allowed to expand. The foams were postcured at 70° C for 15 minutes (foam 2.1), alternatively 60° C for 2 hours (foams 2.2–2.5). Samples were cut and tested in the second exotherm test and the muffle furnace test as described above. Finally the foams were tested in the flash-over test NEN 1076, part C, as described in the specification.

Test results are given in table 2.2.

Table 2.1.

| Foam No. | 2.1 | 2.2 | 2.3 | 2.4 | 2.5 |
|---|---|---|---|---|---|
| Borden TM1 a) | 57.7 | 70 | 70 | | |
| Borden FRD 511 a) | | 30 | 30 | 100 | |
| Borden FRD 530 a) | | | | | 100 |
| Furan resin | 34.0 | | | | |
| Furfurylalcohol | 8.3 | | | | |
| Glucose | 40 | | | | |
| Boric acid | | 20 | 10 | | 20 |
| DC 193 b) | 0.2 | | | | 1 |
| Pluronic f 88 c) | | 1 | 1 | | |
| Dowfax a 11 d) | | | | 4 | |
| Freon 113 e) | 2.5 | 6 | 6 | | 4 |
| Freon 11 e) | | 4 | 4 | | 5 |
| Dimethoxymethane | 1.25 | | | | |
| Dichloromethane | 1.25 | | | | |
| Pentane | | | | 10 | |
| Catalyst: | | | | | |
| o-phosphoric acid, 45 pct | | 6 | 6 | | 5 |
| Tetraphosphoric acid | 7.8 | | | | |
| Isopropanol | 5.8 | | | | |
| Ammoniumchloride, 25 pct | | | | 4 | | a) commercial UFF resins available from Borden Chemical Co., UK.
b) silicone surfactant from Dow.
c) surfactant from BASF, Wyandotte.
d) surfactant from Dow.
e) halogenated hydrocarbons from du Pont.

Table 2.2.

| Foam No. | 2.1 | 2.2 | 2.3 | 2.4 | 2.5 |
|---|---|---|---|---|---|
| Muffle furnace test at | | | | | |
| 550° C flash/burn, sec. | | 16–32 | 8–118 | 6–87 | 10–121 |
| T max. in ° C | | 570 | 595 | 690 | 600 |
| 515°C flash/burn, sec. | | — | 22–120 | 5–183 | 14–123 |
| T max. in ° C | | 530 | 585 | 690 | 575 |
| 508° C flash/burn, sec. | flash + burn | — | 89–132 | 19–157 | — |
| T max. in ° C | | 535 | 565 | 630 | 560 |
| 495° C flash/burn, sec. | | | | 99–131 | |
| T max. in ° C/ | | 570 | | | |
| 2nd exotherm at 200° C max. temp. | 435 | 200 | 210 | | |
| NEN 1076 performance | class 2 | class 1 | class 2 | class 2 | class 1 |
| time to flash over at | | | | | |
| 0.2 cal/cm² sec. | | | | more than 16 min. | |
| 0.4 cal/cm² sec. | 6 min. 45 sec. | more than 16 min. | 7 min. 25 sec. | 1 min. | more than 16 min. |
| 0.6 cal/cm² sec. | | more than 16 min. | | | 4 min. 45 sec. |
| Light transmission | 98 | 97 | 96 | 85 | 98 |

Foam 2.1 contains no boron compound and fails both in muffle furnace test and in the NEN 1076 test.

Foam 2.2 contains 20 parts of boric acid and passes the muffle furnace test both at 525° C and at 508° C and hence also the NEN 1076 test with a very high performance.

Foam 2.3 contains 10 parts of boric acid which with this resin composition gives failure both in the muffle furnace and in the NEN 1076 test.

From the combined results of these two foams we conclude that only a slight increase in boric acid is required to bring foam 2.3 to pass the tests.

Foam 2.4 is made from a resin composition free of furan resin, but even then the fire performance in the absence of a boron compound is very poor.

Foam 2.5 is made from another urea-formaldehyde-furfurylalcohol resin and contains 20 parts boric acid. It passes the muffle furnace test at 508° C and as expected also the NEN 1076 test.

It appears from the results both in example I and example II that there exists a good correlation between the muffle furnace test and the NEN 1076 test.

EXAMPLE III

A foamed material was prepared from a blend consisting of the following ingredients.
Urea-formaldehyde-furfurylalcohol resin 100 parts.
Silicone surfactant 1.5 parts.
Boric acid 15 parts.
n-Pentane 10 parts.

Said urea-formaldehyde-furfurylalcohol resin had an average molar ratio of 1:2.0:0.67. The viscosity was 5400 cp at 25° C.

The blend was pumped into a mixing chamber where it was intimately mixed with 12–13 parts of an acid catalyst consisting of 50% phosphoric acid. The mixture was laid down in a regular pattern into heated moulds 85 × 95 × 10 cm and allowed to rise and cure. After 30 min. in the moulds, the foam blocks were put into a carbinet heated to 50° C with circulating air and left overnight to cure and dry completely.

Samples of 6 × 6 × 6 cm were cut and tested in the second exotherm test (s.e.t.) at 200° C as described in the specification above.

Samples were also tested in the muffle furnace test at 540° C.

Finally the foam was tested in the flash-over test NEN 1076, part C, as described in the specification above.

The test results are stated in table 3.1.

Table 3.1.

| Foam No. | 3.1 | 3.2 |
|---|---|---|
| Maximum temperature second exotherm test at 200° C max. temp. | 210 | 210 |
| Muffle furnace test at 540° C flash | no flash | no flash |
| max. temp. in ° C | 545 | 565 |
| flash-over test NEN 1076, part C, time to flash at 0.40 cal/cm² sec. | more than 30 min. | more than 30 min. |
| time to flash at 0.50 cal/cm² sec. | 6 min. 42 sec. | |
| time to flash at 0.60 cal/cm² sec. | 4 min. 34 sec. | 3 min. 53 sec. |
| Light transmission percent at 0.40 cal/cm² sec. | 99 | 96 |
| Rating | class 1 | class 1 |

Foams 3.1 and 3.2 are equal in composition apart from a slight variation in catalyst contents.

This example shows the use of a resin composition which with 15 parts boric acid will pass the muffle furnace test at a temperature of 540° C.

As expected the foams also passed the NEN 1076 test with good performance.

EXAMPLE IV

A series of foams was prepared using the following formulation.

| | |
|---|---|
| UFF resin (Borden TM1) | x parts |
| Furfurylalcohol prepolymer (Synphrom P490) | y parts |
| where x + y = 100 | |
| Boric acid | z parts |
| Silicone surfactant | 1 part |
| Freon 113 | 6 parts |
| Catalyst 53.5 o/o o-phosphoric acid | 15 parts |
| or 59.4 o/o o-phosphoric acid | 12 parts |

The foams were tested for second exotherm at 200° C and in the muffle furnace at 550° C.

The results are stated in Tables 4.1 – 4.6.

It appeared that in absence of furfurylalcohol prepolymer, an addition of 20 parts by weight boric acid will make the foam pass the muffle furnace test. As the content of furfurylalcohol prepolymer is increased, higher levels of boric acid are required to obtain the desired MFT performance.

The correlation between low second exotherm and no flash-over is evident.

Table 4.1.

| Boric acid | 5 | 10 | 15 | 20 | 25 | 30 | 40 | 50 | 60 |
|---|---|---|---|---|---|---|---|---|---|
| Borden TM1 | 100 | 100 | 100 | 100 | — | 100 | 100 | 100 | 100 |
| Synphorm P490 | — | — | — | — | — | — | — | — | — |
| MFT Flashing 550° C | + | + | + | — | — | — | — | — | — |
| Max.temp. in MFT 550° C | 580 | 580 | 570 | 560 | — | 550 | — | — | 550 |
| Max.temp. in SET 200° C | 220 | 216 | 216 | 213 | — | 211 | — | — | 210 |

Table 4.2.

| Boric acid | 30 |
|---|---|
| Borden TM1 | 95 |
| Synphorm P490 | 5 |
| MFT Flashing 550° C | — |
| Max.temp. in MFT 550° C | 560 |
| Max.temp. in SET 200° C | 212 |

Table 4.3.

| Boric acid | 20 | 25 | 30 | 60 |
|---|---|---|---|---|
| Borden TM1 | 90 | 90 | 90 | 90 |
| Synphorm P490 | 10 | 10 | 10 | 10 |
| MFT Flashing 550° C | + | — | — | — |
| Max.temp. in MFT 550° C | 560 | 570 | 555 | 550 |
| Max.temp. in SET 200° C | 220 | 215 | 211 | 208 |

Table 4.4.

| Boric acid | 20 | 30 | 40 | 60 |
|---|---|---|---|---|
| Borden TM1 | 80 | 80 | 80 | 80 |
| Synphorm P490 | 20 | 20 | 20 | 20 |
| MFT Flashing 550° C | + | — | — | — |
| Max.temp. in MFT 550° C | 590 | 565 | 560 | 560 |
| Max. temp. in SET 200° C | 219 | 211 | 215 | 216 |

Table 4.5.

| Boric acid | 30 | 40 | 50 | 60 |
|---|---|---|---|---|
| Borden TM1 | 70 | 70 | 70 | 70 |
| Synphorm P490 | 30 | 30 | 30 | 30 |
| MFT Flashing 550° C | + | + | — | — |
| Max.temp. in MFT 550°C | 600 | 570 | 570 | 570 |

-continued

| | | | | |
|---|---|---|---|---|
| Max.temp. in SET 200° C | 213 | 226 | 220 | 221 |

Table 4.6.

| | | | |
|---|---|---|---|
| Boric acid | 30 | 50 | 60 |
| Borden TM1 | 60 | 60 | 60 |
| Synphorm P490 | 40 | 40 | 40 |
| MFT Flashing 550° C | + | + | + |
| Max.temp. in MFT 550° C | 610 | 610 | 615 |
| Max.temp. in SET 200° C | 223 | 222 | 253 |

EXAMPLE V

Foams were prepared using the well-known technique of preparing a ureaformaldehyde foam from an aqueous solution of a commercial ureaformaldehyde resin (vide U.S. Pat. No. 3,006,871). 100 parts of a UF resin (Urecoll 270, BASF) were dissolved in 100 parts of water. Foams were made using this solution and the formulations stated below.

Table 5.1.

| Foam No. | 5.1 | 5.2 | 5.3 | 5.4 |
|---|---|---|---|---|
| Urecoll 270/H20 1:1 | 200 | 200 | 150 | 300 [1] |
| Water | 100 | 100 | 50 | — |
| Surfactant | 3 | 3 | 2.5 | 2 |
| Furfurylalcohol | 50 | 50 | 25 | 25 |
| Boric acid | | | 30 | 30 |
| 9.7 o/o aq $H_3PO_4$ | 50 | 50 | 50 | 20 |
| MFT (550° C) flash +/− | + | + | + | + |
| MFT (550° C) T max. ° C | 660 | 715 | 590 | 670 |

[1] 2 parts Urecoll 270 dissolved in 4 parts water.

It appears, that all foams fail in the MFT and the high temperatures recorded in the test show that a sufficient degree of cure has not been achieved by using this technique of foam preparation.

In such cases the addition of boric acid is not able to remove the flash-over from the foam.

EXAMPLE VI

A foam was prepared using a commercial ureaformaldehyde resin (Urecoll 270, BASF) dissolved in furfurylalcohol. 40 parts of Urecoll 270 were dissolved in 60 parts of furfurylalcohol.

To 100 parts of this solution were added
10 parts of water
1 parts of a surfactant (DC 193)
30 parts of boric acid
2 parts of Freon 113 and as a catalyst
64 parts of an aq o-$H_3PO_4$ solution (59 o/o w/w).

The foam was allowed to rise and cure. When tested in the muffle furnace test (550° C) the foam did not flash, the maximum temperature recorded was 575° C.

EXAMPLE VII

The following example is intended to show that the addition of boric acid in itself is not sufficient to render a foam non-flashing, although the particular foam showed no second exotherm. The foam must also be prepared from ureaformaldehyde and furfurylalcohol.

A polyurethane foam was prepared by reacting 50 parts of a commercial polyether polyol RF 33 from Lancro Chemicals with 70 parts of a polyisocyanate in the presence of 15 parts blowing agent and the usual surfactant and catalyst additives. The foam had a density of 35 kg/m³ and had no second exotherm and showed a vigorous burning with heavy smoke in the 550° C muffle furnace test.

A similar foam was prepared with the addition of 30 parts of boric acid. The foam had a density of 21.5 kg/m³, had no exotherm, and burned violently in the muffle furnace test, both at 550° and at 500° C.

EXAMPLE VIII

A ureaformaldehyde furfurylalcohol (UFF) resin was prepared according to example 1 of British patent 942,845. From this resin foams were prepared according to the formulations stated in Table 8.1, which also contains test results.

Table 8.1.

| Foam | 8.1 | 8.2 | 8.3 | 8.4 |
|---|---|---|---|---|
| UFF resin | 100 | 100 | 100 | 100 |
| Furfurylalcohol | — | — | — | 5 |
| Surfactant DC 193 | 1 | 1 | 111 | 1 |
| Water | — | — | — | 5 |
| Freon 113 | 1 | 1 | — | — |
| Sodiumbicarbonate | — | — | 6 | 5 |
| Boric acid | — | 30 | — | 30 |
| o-$H_3PO_4$, 59 o/o aq soln | 12 | 15 | | |
| c-$H_3PO_4$, 66,5 o/o aq soln | | | 22 | 22 |
| Muffle furnace test (550° C), flash +/− | + | — | + | — |
| Max. temp. ° C | 640 | 560 | 690 | 575 |
| 2nd exotherm test (200° C)° C | | 206 | 208 | 204 |

It appears that only foams containing boric acid and having no second exotherm at 200° C will pass the muffle furnace test at 550° C.

EXAMPLE IX

A ureaformaldehyde furfurylalcohol (UFF) resin was prepared according to British patent 1,248,756 having a U:F:F molar ratio = 1:3:0.6. Foams were prepared using this resin in the formulations stated in Table 9.1, which also contains test results.

Table 9.1.

| Foam No. | 9.1 | 9.2 | 9.3 |
|---|---|---|---|
| UFF resin | 100 | 100 | 100 |
| Furfurylalcohol | 20 | 30 | 40 |
| Boric acid | 36 | 59 | 42.5 |
| Surfactant (DC 193) | 1.2 | 1.3 | 1.45 |
| Blowing agent (Freon 113) | 1.2 | 1.3 | 1.45 |
| o-$H_3PO_4$, 89 o/o | 9.6 | 6 | 6 |
| Water | 4.8 | 3 | 3 |
| 2nd exotherm test at 200° C, max. temp. ° C | 211 | 208 | 211 |
| Muffle furnace test at 550° C, flash +/− | — | — | — |
| Max. temp. ° C | 600 | 595 | 605 |

All foams were free of second exotherm and pass the muffle furnace test.

EXAMPLE X

A ureaformaldehyde furfurylalcohol (UFF) resin was prepared according to British patent 1,248,756, having a u:f:f molar ratio = 1:3:1. From this resin foams were made using the formulations stated in Table 10.1. Test results are stated in the table.

Table 10.1.

| Foam No. | 10.1 | 10.2 | 10.3 | 10.4 |
|---|---|---|---|---|
| UFF resin | 100 | 100 | 100 | 100 |
| Surfactant (DC 193) | 1 | 1 | 1 | 1 |
| Freon 113 | 1 | 1 | 1 | 1 |
| Boric acid | 30 | 10 | — | 30 |
| Glucose | | | 20 | |
| Catalyst: | | | | |
| o-H$_3$PO$_4$, 89 o/o, parts by weight | 8 | 8 | 8 | 8 |
| Water | 4 | 4 | 4 | 4 |
| Glucose | — | — | — | 10 |
| 2nd exotherm test (200° C), max. temp. (° C) | 208 | 208 | 225 | 206 |
| Muffle furnace test (550° C), flash +/− | — | + | + | — |
| Max. temp., ° C | 585 | 580 | 715 | 600 |

The foams containing 30 parts of boric acid and having no second exotherm at 200° C pass the muffle furnace test.

EXAMPLE XI

Foams were prepared using a resin similar to the one used in example X, but having a U:F:F molar ratio = 1:3:2.

Table 11.1 contains the formulations used and the test results.

Table 11.1.

| Foam No. | 11.1 | 11.2 |
|---|---|---|
| UFF resin | 100 | 100 |
| Surfactant (DC 193) | 1 | 1 |
| Blowingagent (Freon 113) | 1 | 1 |
| Boric acid | — | 30 |
| Catalyst: | | |
| o-H$_3$PO$_4$, 89 o/o, parts by weight | 8 | 8 |
| Water | 4 | 4 |
| Glucose | | 10 |
| 2nd exotherm test, (20° C) ° C | 219 | 210 |
| Muffle furnace test 550° C, flash +− | + | — |
| Max. temp., ° C | 555 | 560 |

EXAMPLE XII

Preparation of glyoxal-boric acid complex:
193.5 g of 30 w.w. percent aqueous glyoxal (1 mole) was blended with
61.8 g boric acid (1 mole) and heated to 85°–90° C for 1 hour and cooled to room temperature.
White precipitate was formed, which was filtered, washed and dried. Yield was 68.3 g.
Four foams were prepared using the following formulation:
100 parts ureaformaldehyde furfurylalcohol resin with an average molar ratio of 1 to 1.8 to 0.6.
1.5 parts silicone surfactant (Dow Corning 193).
10 parts n-pentane,
25 parts boron compound, and
12–17 parts catalyst containing 50% phosphoric acid.
Type of boron compound and test results are shown in Table 12.1.

Table 12.1.

| Foam No. | 12.1 | 12.2 | 12.3 | 12.4 |
|---|---|---|---|---|
| Trimethoxylboroxine | 25 | | | |
| Sodiumtetraborate | | 12.5 | | |
| Boric acid | | 12.5 | | |
| Glyoxal/boric acid complex | | | 25 | |
| Second exotherm at 200° C | 205 | 215 | 207 | 212 |
| Muffle furnace test 505° C, flash +/− | — | — | — | + |
| Max. temp. during test, in ° C | 540 | 515 | 505 | 532 |

Foam 12.4, which contains no boron compound, is included as a control. It flashes and burns in the muffle furnace test and will not pass the NEN 1076 test. The other foams show no burning in the muffle furnace and will pass the NEN 1076 test.

EXAMPLE XIII

Foams were prepared using a resin similar to the one used in example X, but having a U:F:F molar ratio = 1:3:6.

Table 13.1 contains the formulations used and the test results.

Table 13.1.

| Foam No. | 13.1 | 13.2 |
|---|---|---|
| UFF resin | 100 | 100 |
| Surfactant (DC 193) | 1 | 1 |
| Freon 113 | 1 | 1 |
| Boric acid | — | 30 |
| Glucose | 20 | |
| Catalyst: | | |
| o/H$_3$PO$_4$, 89 o/o, parts by weight | 8 | 8 |
| Water | 4 | 4 |
| Glucose, dissolved | | 10 |
| 2nd exotherm test (200° C), ° C | 223 | 210 |
| Muffle furnace test 550° C, flash +/− | + | — |
| Max. temp., ° C | 740 | 580 |

EXAMPLE XIV

A series of foams was made by reacting 100 parts of a commercial ureaformaldehyde furfurylalcohol resin (Borden TM1) with 1 part of a surfactant (DC 193), and 6 parts of a blowing agent (1.1.1-trichloroethane : dichloroethane 1:2) in the presence of 10 parts of a catalyst consisting of ortho-phosphoric acid (specific gravity 1.5). In addition the formulations contain filler and/or water as stated in Table 14.1.

In foam 11–17 the 10 parts of o-H$_3$PO$_4$ (s.g. 1.5) were replaced by 9 parts H$_2$SO$_4$ (6 n).

Table 14.1

| Foam No. | 14.1 | 14.2 | 14.3 | 14.4 | 14.5 | 14.6 | 14.7 | 14.8 |
|---|---|---|---|---|---|---|---|---|
| Boric acid | 30 | — | — | — | 20 | — | — | 10 |
| Glucose | — | — | 30 | 20 | — | — | 10 | — |
| Talc | — | 30 | — | — | — | 20 | — | — |
| Water | | | | | | | | |
| Muffle furnace test 550° C, flash +/− | — | + | + | + | + | + | + | + |
| Max. temp., ° C | 555 | 675 | 700 | 670 | 550 | 670 | 665 | 625 |

| Foam No. | 14.9 | 14.10 | 14.11 | 14.12 | 14.13 | 14.14 | 14.15 | 14.16 | 14.17 |
|---|---|---|---|---|---|---|---|---|---|
| Boric acid | — | 30 | 30 | 30 | 30 | — | — | — | 30 |
| Glucose | — | — | — | — | — | 30 | — | — | — |
| Talc | 10 | — | — | — | — | — | 30 | — | — |
| Water | — | 4 | 6 | 8 | 2 | 4 | 4 | — | — |
| Muffle furnace test | | | | | | | | | |

Table 14.1-continued

| 350° C, flash +/− | + | − | − | − | − | + | + | + | − |
|---|---|---|---|---|---|---|---|---|---|
| Max.temp., °C | 635 | 585 | 560 | 570 | 560 | 700 | 690 | 700 | 570 |

It appears that foams containing 30 parts of boric acid pass the muffle furnace test.

What we claim is:

1. A method of preparing foamed solid aminoformaldehyde furfurylalcohol products by polymerizing a liquid furfurylalcohol containing aminoformaldehyde resin composition in the presence of an acid, characterized in using as a starting material a resin composition containing 15–90% by weight of total free and bound furfurylalcohol and having an urea: formaldehyde molar ratio of 1:1 to 1:5 and at least 10 parts by weight of a boron compound per 100 parts by weight of said resin, the boron compound being present in an amount sufficient so that the foam product will pass the muffle furnace test at 500° C., and has no second exotherm at 200° C., said boron compound being selected from the group consisting of boric acid, boron oxide, borax, boric acid esters, boron tribromide, boron trichloride, boron nitride, boron phosphate, boron trifluoride etherate, boron trifluoride methanol, boron trifluoride monoethylamine, complexes of boric acid with polyhydroxyl compounds, and mixtures thereof.

2. A method according to claim 1, characterized in using a resin composition, which when foamed in absence of a boron compound, has no second exotherm at 200° C.

3. A method according to claim 1, characterized in using a resin composition, which when foamed in the presence of at least 10 parts by weight of a boron compound per 100 parts by weight of resin, has no second exotherm at 200° C.

4. A method according to claim 1, characterized in using a resin composition containing 25 to 70% by weight of total free and bound furfurylalcohol and a urea:formaldehyde molar ratio of from 1:1.5 to 1:4.

5. A method according to claim 1, characterized in using a resin composition containing 25 to 50% by weight of total free and bound furfurylalcohol and a urea:formaldehyde molar ratio of from 1:1.5 to 1:2.5.

6. A method according to claim 1, characterized in using a resin composition containing 30 to 40% by weight of total free and bound furfurylalcohol and a urea:formaldehyde molar ratio of from 1:1.7 to 1:2.1.

7. A method according to claim 1 characterized in using boric acid as the boron compound.

8. A method according to claim 1, characterized in using 10 to 60 parts by weight of a boron compound per 100 parts by weight of resin.

9. Foamed products, prepared according to claim 1.

* * * * *